(12) United States Patent
Kang et al.

(10) Patent No.: US 10,617,316 B2
(45) Date of Patent: Apr. 14, 2020

(54) DETACHABLE BIOSIGNAL COMPLEX SENSOR AND METHOD OF DETECTING BIOSIGNAL INFORMATION USING THE SAME

(71) Applicant: SAMSUNG ELECTRONICS CO., LTD., Suwon-si (KR)

(72) Inventors: Jaemin Kang, Seoul (KR); Yongjoo Kwon, Yongin-si (KR); Sunkwon Kim, Suwon-si (KR); Younho Kim, Hwaseong-si (KR); Sangyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1022 days.

(21) Appl. No.: 14/804,518

(22) Filed: Jul. 21, 2015

(65) Prior Publication Data

US 2016/0106333 A1 Apr. 21, 2016

(30) Foreign Application Priority Data

Oct. 15, 2014 (KR) .................. 10-2014-0139068

(51) Int. Cl.
| | | |
|---|---|---|
| *A61B 5/0408* | (2006.01) | |
| *A61B 5/00* | (2006.01) | |
| *A61B 5/02* | (2006.01) | |
| *A61B 5/026* | (2006.01) | |
| *A61B 5/053* | (2006.01) | |
| *A61B 5/021* | (2006.01) | |
| *A61B 5/0205* | (2006.01) | |

(Continued)

(52) U.S. Cl.
CPC ........ *A61B 5/04085* (2013.01); *A61B 5/0059* (2013.01); *A61B 5/021* (2013.01); *A61B 5/026* (2013.01); *A61B 5/02007* (2013.01); *A61B 5/0537* (2013.01); *A61B 5/681* (2013.01); *A61B 5/0205* (2013.01); *A61B 5/0285* (2013.01); *A61B 5/14551* (2013.01)

(58) Field of Classification Search
CPC ... A61B 5/04085; A61B 5/6801; A61B 5/681; A61B 5/6824
See application file for complete search history.

(56) References Cited

U.S. PATENT DOCUMENTS

| | | | |
|---|---|---|---|
| 6,171,242 B1 * | 1/2001 | Amano | ............... A61B 5/02 600/423 |
| 8,725,842 B1 | 5/2014 | Al-Nasser | |

(Continued)

FOREIGN PATENT DOCUMENTS

| | | |
|---|---|---|
| KR | 20-2012-0008484 U | 12/2012 |
| KR | 10-2013-0024468 A | 3/2013 |
| KR | 10-2013-0138421 A | 12/2013 |

*Primary Examiner* — John R Downey
(74) *Attorney, Agent, or Firm* — Sughrue Mion, PLLC

(57) ABSTRACT

A detachable biosignal complex sensor includes a clip type structure including: a circuit module configured to receive a biosignal of a subject and perform signal processing on the biosignal, a first plate, and a second plate having an end thereof which is rotatably connected to an end of the first plate so that the clip type structure is configured to be fastened to an item; and a sensor and electrodes provided on outer surfaces of the first plate and the second plate and configured to obtain the biosignal and transmit the obtained biosignal to the circuit module.

15 Claims, 14 Drawing Sheets

(51) Int. Cl.
*A61B 5/0285* (2006.01)
*A61B 5/1455* (2006.01)

(56) References Cited

U.S. PATENT DOCUMENTS

| | | | | |
|---|---|---|---|---|
| 2002/0177781 | A1* | 11/2002 | Amano | A61B 5/021 |
| | | | | 600/485 |
| 2006/0047327 | A1* | 3/2006 | Colvin | A61B 5/076 |
| | | | | 607/60 |
| 2006/0083115 | A1* | 4/2006 | Lafever | G04B 37/1486 |
| | | | | 368/282 |
| 2006/0288233 | A1* | 12/2006 | Kozlay | G06F 21/32 |
| | | | | 713/186 |
| 2007/0135264 | A1* | 6/2007 | Rosenberg | A63B 24/0062 |
| | | | | 482/8 |
| 2007/0191718 | A1* | 8/2007 | Nakamura | A61B 5/0002 |
| | | | | 600/503 |
| 2007/0279852 | A1* | 12/2007 | Daniel | A44C 5/0007 |
| | | | | 361/679.03 |
| 2008/0114217 | A1* | 5/2008 | Suyama | A61B 5/02055 |
| | | | | 600/300 |
| 2010/0132237 | A1* | 6/2010 | McDermott | G09F 3/005 |
| | | | | 40/633 |
| 2014/0200412 | A1 | 7/2014 | Martinez et al. | |
| 2014/0257049 | A1* | 9/2014 | Soundarapandian | A61B 5/681 |
| | | | | 600/301 |
| 2015/0117161 | A1* | 4/2015 | Nichol | G04B 47/063 |
| | | | | 368/10 |
| 2015/0135310 | A1* | 5/2015 | Lee | A61B 5/681 |
| | | | | 726/20 |
| 2015/0297134 | A1* | 10/2015 | Albert | A61B 5/681 |
| | | | | 600/384 |
| 2016/0058331 | A1* | 3/2016 | Keen | G06F 9/542 |
| | | | | 600/595 |

* cited by examiner

DETACHABLE BIOSIGNAL COMPLEX SENSOR AND METHOD OF DETECTING BIOSIGNAL INFORMATION USING THE SAME

CROSS-REFERENCE TO RELATED APPLICATION

This application claims the benefit of Korean Patent Application No. 10-2014-0139068, filed on Oct. 15, 2014, in the Korean Intellectual Property Office, the disclosure of which is incorporated herein in its entirety by reference.

BACKGROUND

1. Field

The exemplary embodiments relate to detachable biosignal complex sensors and methods of detecting biosignal information using the same.

2. Description of the Related Art

With the advances in medicine and increased lifespan of people, interest in health care has increased. Accordingly, interest in medical appliances has also increased. Examples of such medical appliances include various medical appliances used in hospitals or clinics, small- and medium-sized medical appliances installed in public institutions or the like, and small-sized medical appliances and health care devices that may be individually owned or used.

Regarding medical appliances or medial examinations, an invasive measurement method has been widely used. For example, when an invasive measurement method is used, a blood sample is collected from a subject and blood analysis is performed on the collected blood sample. However, such an invasive measurement method may be painful and inconvenient to use due to the need to employ a reagent that reacts with a specific substance in blood and a colorimetric assay and optical device.

SUMMARY

Exemplary embodiments may provide detachable biosignal complex sensors and methods of detecting biosignal information using the same.

Additional aspects will be set forth in part in the description which follows and, in part, will be apparent from the description, or may be learned by practice of the presented exemplary embodiments.

According to an aspect of an exemplary embodiment, there is provided a detachable biosignal complex sensor including: a clip type structure including a circuit module configured to receive a biosignal of a subject and perform signal processing on the biosignal, a first plate, and a second plate having an end thereof which is rotatably connected to an end of the first plate so that the clip type structure is configured to be fastened to an item; and a sensor and electrodes provided on outer surfaces of the first plate and the second plate and configured to obtain the biosignal and transmit the obtained biosignal to the circuit module.

The electrodes may include: a first electrode and a second electrode on the first plate; and a third electrode and a fourth electrode on the second plate.

The first electrode and the second electrode may be configured to function as an electrocardiogram sensor, and the first electrode, the second electrode, the third electrode, and the fourth electrode may be configured to function as a body fat sensor.

The sensor may be a blood pressure sensor provided on the first plate.

The blood pressure sensor may include a light-emitting element configured to emit light and a light-receiving element configured to receive light, wherein the biosignal is obtained based on the emitted and received light.

The blood pressure sensor may include a light-receiving element configured to receive light, and a first light-emitting element and a second light-emitting element which are respectively positioned on opposite sides of the light-emitting element and configured to emit light, wherein the biosignal is obtained based on the emitted and received light.

The first electrode and the second electrode may be spaced apart from each other in a first direction, and the first light-emitting element, the light-receiving element, and the second light-emitting element may be spaced apart from one another between the first electrode and the second electrode in a second direction perpendicular to the first direction.

The clip type structure may include a flexible material.

The detachable biosignal complex sensor may further include a pair of connection members respectively provided at other ends of the first plate and the second plate, the other ends being opposite to the ends at which the first plate and the second plate are connected.

The pair of connection members may include a magnet and magnetic material or male and female Velcro® parts.

The circuit module may include: a personal authenticator configured to perform personal authentication based on an electrocardiogram signal of the subject and thereby generate personal-authenticated user information; and a biosignal information analyzer configured to analyze biosignal information of the subject by using the personal-authenticated user information and the biosignal.

The detachable biosignal complex sensor may further include a communicator configured to output an analysis result of the biosignal information analyzer to an external device.

According to another exemplary embodiment, there is provided a biosignal information detection system including: any one of the above-described detachable biosignal complex sensors according to an exemplary embodiment; and an external electronic device including a user interface configured to receive an execution command which commands the detachable biosignal complex sensor to execute a process and outputs a command execution result of the process, and a communicator configured to communicate with the detachable biosignal complex sensor.

The circuit module of the detachable biosignal complex sensor may include: a personal authenticator configured to perform personal authentication based on an electrocardiogram signal of the subject and thereby generate personal-authenticated user information; and a biosignal information analyzer configured to analyze biosignal information of the subject by using personal-authenticated user information and the biosignal.

The external electronic device may include: a personal authenticator configured to perform personal authentication based on an electrocardiogram signal of the subject and thereby generate personal-authenticated user information; and a biosignal information analyzer configured to analyze biosignal information of the subject by using the personal-authenticated user information and the biosignal.

According to another exemplary embodiment, there is provided a method of detecting a biosignal including: attaching one of the above-described detachable biosignal complex sensors according to an exemplary embodiment to an item of a subject; performing personal authentication to determine whether the subject is a registered user of the detachable biosignal complex sensor; and acquiring the biosignal from the subject through the sensor and the electrodes, and analyzing biosignal information of the subject based on the acquired biosignal, according to whether the personal authentication indicates that the subject is the registered user.

The item includes a wrist watch.

The electrodes may include a first electrode, a second electrode, a third electrode, and a fourth electrode. The first electrode and the second electrode may be configured to detect an electrocardiogram signal. The first electrode, the second electrode, the third electrode, and the fourth may be configured to detect body fat.

The performing of the personal authentication may include using the electrocardiogram signal detected by the first electrode and the second electrode to determine whether the subject is the registered user.

The biosignal information may include one of a body composition, an electrocardiogram, a vascular compliance, a blood flow rate, arterial stiffness, a systolic blood pressure, or a diastolic blood pressure.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1A:
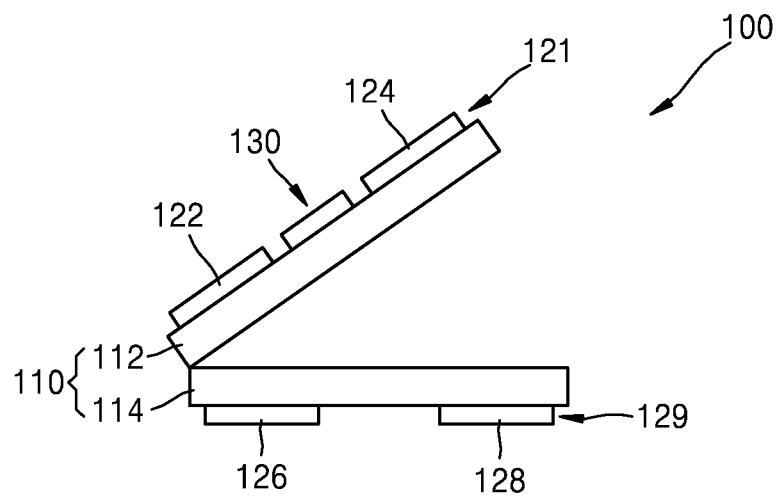
FIGS. 1A and 1B are cross-sectional views of a detachable biosignal complex sensor according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the exemplary embodiments. As used herein, the term "and/or" includes any and all combinations of one or more of the associated listed items.

It will be understood that when a layer, region, or component is referred to as being "formed on," another layer, region, or component, the layer, region, or component can be directly or indirectly formed on the other layer, region, or component. That is, for example, intervening layers, regions, or components may be present.

It will be understood that, although the terms "first", "second", etc., may be used herein to describe various elements, these elements should not be limited by these terms. These terms are only used to distinguish one element from another.

The terminology used herein is for the purpose of describing particular exemplary embodiments only and is not intended to be limiting of the exemplary embodiments. As used herein, the singular forms "a", "an", and "the" are intended to include the plural forms as well, unless the context clearly indicates otherwise.

In addition, the terms "unit" and "module" may refer to a unit configured to process at least one function or operation and the "unit" and "module" may be implemented by hardware, software, or a combination thereof.

Figure 1B:
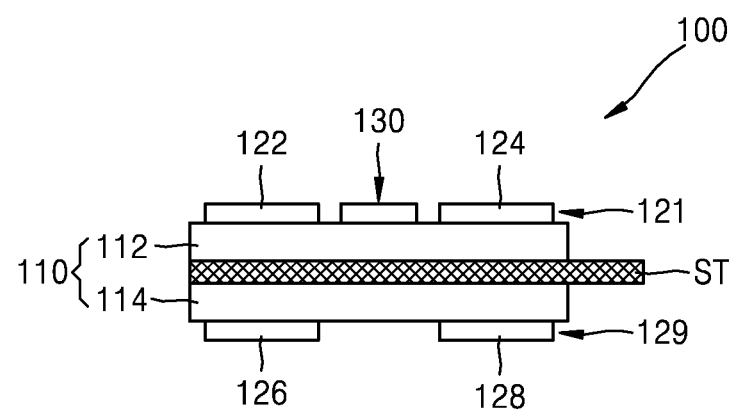
Figure 2A:
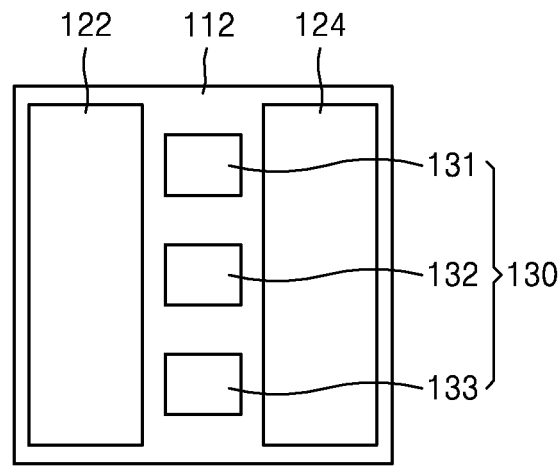
FIGS. 2A and 2B are plan views, respectively, illustrating a first plate and a second plate in a detachable biosignal complex sensor according to an exemplary embodiment.
Figure 2B:
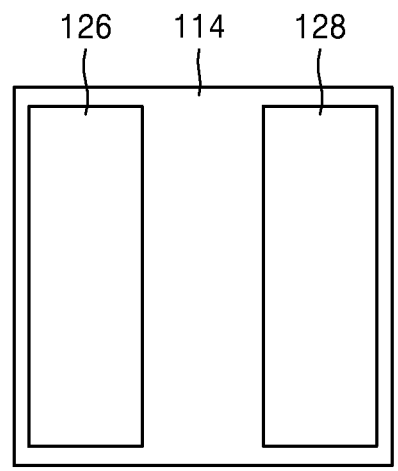

FIGS. 1A and 1B are cross-sectional views of a detachable biosignal complex sensor 100 according to an exemplary embodiment. Specifically, FIG. 1A illustrates a case where a clip type structure 110 is opened, and FIG. 1B illustrates a case where the clip type structure 110 is attached to a strap ST. FIGS. 2A and 2B are plan views, respectively, illustrating a first plate 112 and a second plate 114 in the detachable biosignal complex sensor 100 according to the exemplary embodiment.

The detachable biosignal complex sensor 100 may sense a biosignal from a subject and analyze biosignal information by using the sensed biosignal.

According to an exemplary embodiment, the term subject refers to an object from which biosignal information is to be detected. The subject may be a living body portion that can come in contact with the detachable biosignal complex sensor 100 or be placed adjacent to the detachable biosignal complex sensor 100. For example, the subject may be a living body portion from which a pulse wave or body fat is easily measured through photoplethysmography (PPG). For example, the subject may be a surface of a wrist. However, the subject is not limited thereto.

The biosignal information is unique information of the subject. For example, the biosignal information may be a signal based on a movement of a specific object (for example, a heart or a muscle) of the subject, such as an electrocardiogram (ECG), a ballistocardiogram (BCG), a photoplethysmograph (PPG), or an electromyogram (EMG), the biosignal information may be a blood pressure, and the biosignal information may be information on an amount of materials included in the subject, for example, a blood sugar, a cholesterol, and body fat.

Also, in the following exemplary description, a "user" may be a subject from which biosignal information is to be measured, but the user may also be a medical expert capable of using the detachable biosignal complex sensor 100. That is, the term "user" according to an exemplary embodiment may refer to many types of people in addition to the subject.

Referring to FIGS. 1A and 1B, the detachable biosignal complex sensor 100 may include a clip type structure 110, a blood pressure sensor 130 disposed on an outer surface of the clip type structure 110, and a plurality of electrodes 122, 124, 126, and 128.

The clip type structure 110 may include a built-in circuit module (CM) that senses a biosignal from a subject and performs signal processing on the sensed biosignal. The clip type structure 110 may include a first plate 112 and a second plate 114. One end of the first plate 112 and one end of the second plate 114 are rotatably connected together to form a pair of claws. Thus, items (e.g., straps, clothing, etc.) placed between the first plate 112 and second plate 114 may be caught between the first plate 112 and the second plate 114 when the first and second plates 114 are rotated in such a way to close the first and second plates 112 and 114 on the item.

As illustrated in FIG. 1A, a gap between the first plate 112 and the second plate 114 of the clip type structure 110 may be opened. Also, as illustrated in FIG. 1B, a gap between the first plate 112 and the second plate 114 of the clip type structure 110 may be closed with a strap ST disposed therebetween. The strap ST may be a watch strap of a wrist watch, a belt, or a waist portion of pants.

The first plate 112 and the second plate 114 may be made of a plastic material, a flexible polymer material, or a stretchable polymer material. For example, the first plate 112 and the second plate 114 may be made of a material selected from the group of poly(dimetylsiloxane)(PDMS), poly vinyl alcohol (PVA), polyurethane, polyurethane acrylate (PUA), poly(styrene-isoprene-styrene)(SIS), poly(styrene-butadiene-styrene)(SBS), (poly(styrene-ethylene/butylene-styrene) (SEBS), polyvinylidenefluoride (PVDF), nitrile butadiene rubber (NBR), perfluoropolyether (PFPE), and polyester (PE).

Referring to FIG. 2A, the first electrode 122, the second electrode 124, and the blood pressure sensor 130 are disposed on the first plate 112. Specifically, the first electrode 122, the second electrode 124, and the blood pressure sensor 130 are disposed on one surface of the first plate 112 that is the outer surface of the clip type structure 110.

The first electrode 122 and the second electrode 124 may act as an ECG sensor. The ECG sensor 121 is configured to sense electrical activity of a heart. The ECG sensor 121 may detect a slight electrical signal that is sensed from a person's skin when myocardium is depolarized at every heartbeat. At the same time, the first electrode 122 and the second electrode 124 may also act as a part of a body fat sensor 129.

The blood pressure sensor 130 may be disposed between the first electrode 122 and the second electrode 124. The blood pressure sensor 130 may include light-emitting elements 131 and 133 and a light-receiving element 132. Specifically, the blood pressure sensor 130 may include the light-receiving element 132, and the first light-emitting element 131 and the second light-emitting element 133 disposed at opposite sides of the light-receiving element 132. However, the number of the light-emitting elements and the light-receiving elements shown in FIG. 2A are merely exemplary. The blood pressure sensor 130 may include a single light-emitting element, or may include two or more light-emitting elements. In addition, the blood pressure sensor 130 may include a plurality of light-receiving elements.

The first electrode 122 and the second electrode 124 may be spaced apart from each other in a predetermined direction, and the first light-emitting element 131, the light-receiving element 132, and the second light-emitting element 133 may be spaced apart from one another in a direction perpendicular to the predetermined direction. However, such an arrangement is only for illustrative purposes and the exemplary embodiments are not limited thereto.

As the first and second light-emitting elements 131 and 133, light-emitting diodes (LEDs) or laser diodes (LDs) may be used, although exemplary embodiments are not limited thereto. As the light-receiving element 132, a photo diode (PD), a photo transistor (PTr), or a charge-coupled device (CCD) may be used, although exemplary embodiments are not limited thereto.

The first and second light-emitting elements 131 and 133 may irradiate light on the subject, and the light-receiving element 132 may sense an optical signal that is scattered or reflected from the subject. The sensed optical signal may be used for pulse wave analysis, and a variety of biosignal information may be analyzed from the sensed optical signal.

Referring to FIG. 2B, the third electrode 126 and the fourth electrode 128 are disposed on the second plate 114. Specifically, the third electrode 126 and the fourth electrode 128 may be disposed on one surface of the second plate 114 that is the outer surface of the clip type structure 110.

The third electrode 126 and the fourth electrode 128, together with the first electrode 122 and the second electrode 124, may constitute a body fat sensor. The body fat sensor may measure body fat based on bioelectrical impedance analysis (BIA). BIA is a method of calculating a ratio of body fat content and body water content by using a difference in electrical resistance between non-fat tissue and fat tissue when an AC wave having low energy passes through a body. That is, BIA allows current to flow through the body by taking into account that the body is a combination of impedances, measures a voltage through the current, and measures the impedance of the body based on the current and the voltage. In this manner, BIA may analyze body composition. The plurality of electrodes 122, 124, 126, and 128 come into contact with the subject. Of the plurality of electrodes 122, 124, 126, and 128, the two electrodes, for example, the first and third electrodes 122 and 126, may serve as input electrodes for the input of the current, and the remaining electrodes, for example, the second and fourth electrodes 124 and 128, may serve as output electrodes for the detection of the voltage. However, this description is merely exemplary, and other electrodes among the plurality of electrodes 122, 124, 126 and 128 may function as the input electrodes and the output electrodes in various combinations.

Figure 3A:
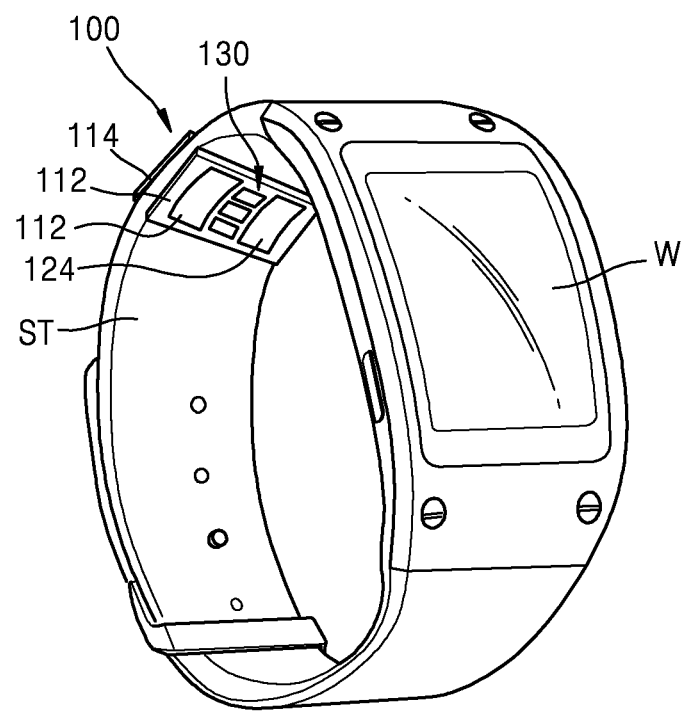
FIGS. 3A and 3B are perspective views, respectively, illustrating an inner side and an outer side of a strap of a wrist watch as an example in which a detachable biosignal complex sensor according to an exemplary embodiment is attached to the wrist watch.
Figure 3B:
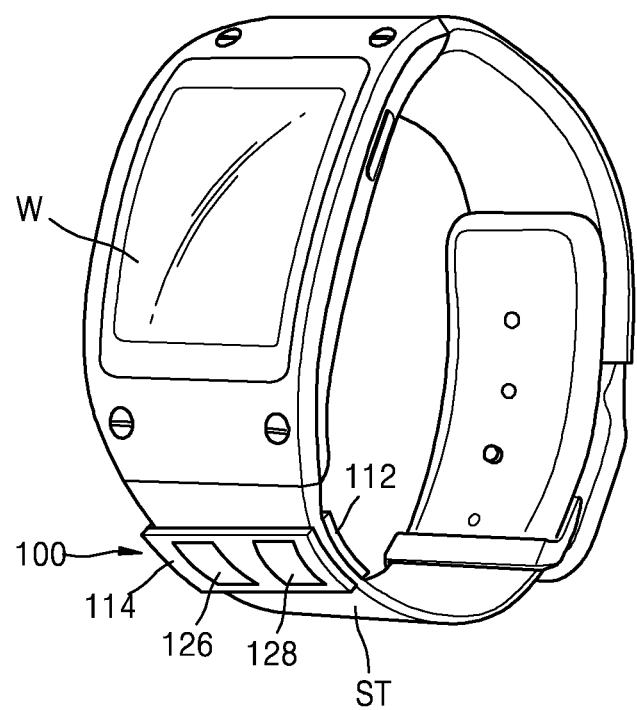

FIGS. 3A and 3B are perspective views illustrating an example in which the detachable biosignal complex sensor 100 according to the exemplary embodiment is attached to a wrist watch W. Specifically, FIGS. 3A and 3B are perspective views, respectively, illustrating the inner surface and the outer surface of the strap ST of the wrist watch W.

Referring to FIG. 3A, the detachable biosignal complex sensor 100 is attached such that the first plate 112 is disposed on the inner surface of the strap ST of the wrist watch W. That is, the first and second electrodes 122 and 124, which may serve as the ECG sensor and the body fat sensor, and the first and second light-emitting elements 131 and 133 and the light-receiving element 132, which constitute the blood pressure sensor 130, come into contact with the wrist of the user who wears the wrist watch W.

Referring to FIG. 3B, the detachable biosignal complex sensor 100 is attached such that the second plate 114 is disposed on the outer surface of the strap ST of the wrist watch W. The third and fourth electrodes 126 and 128, which may serve as elements of the body fat sensor 129, are exposed to the outside.

Figure 4A:
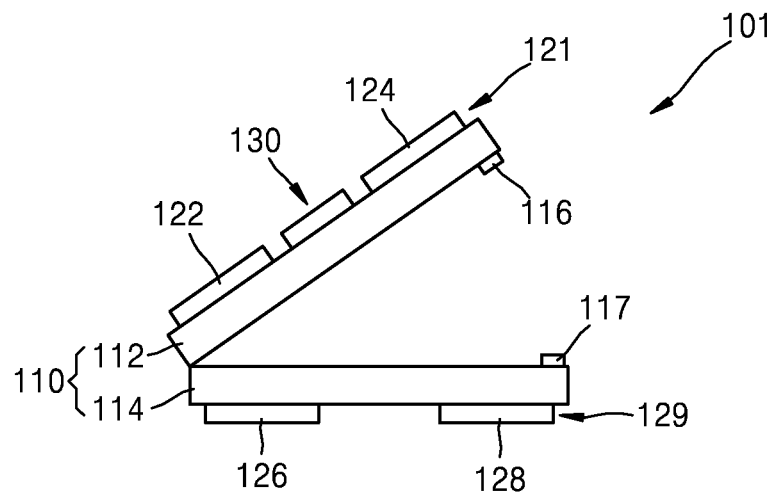
FIGS. 4A and 4B are cross-sectional views of a detachable biosignal complex sensor according to another exemplary embodiment.
Figure 4B:
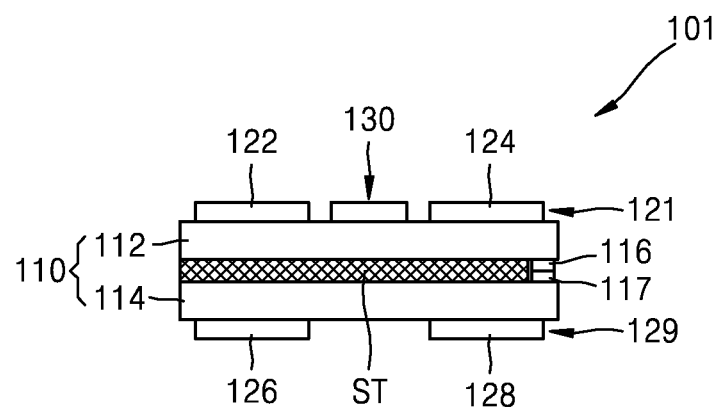

FIGS. 4A and 4B are cross-sectional views of a detachable biosignal complex sensor 101 according to another exemplary embodiment. Specifically, FIG. 4A illustrates a case where a clip type structure 110 is opened, and FIG. 4B illustrates a case where the clip type structure 110 is attached to a strap ST.

The detachable biosignal complex sensor 101 of FIGS. 4A and 4B differs from the detachable biosignal complex sensor 100 of FIGS. 1A and 1B in that a pair of connection members 116 and 117 are further provided at one end of a first plate 112 and one end of a second plate 114, respectively. In the clip type structure 110, the connection members 116 and 117 may be provided at the other ends opposite to the ends to which the first plate 112 and the second plate 114 are connected. The connection members 116 and 117 may serve to stably maintain a state in which the strap ST is disposed between the first plate 112 and the second plate 114. Examples of the connection members 116 and 117 may include magnet and magnetic material, or male and female Velcro® parts (e.g., hooks and loops). However, the connection members 116 and 117 are not limited thereto and various type of connection members may be implemented.

Figure 5:
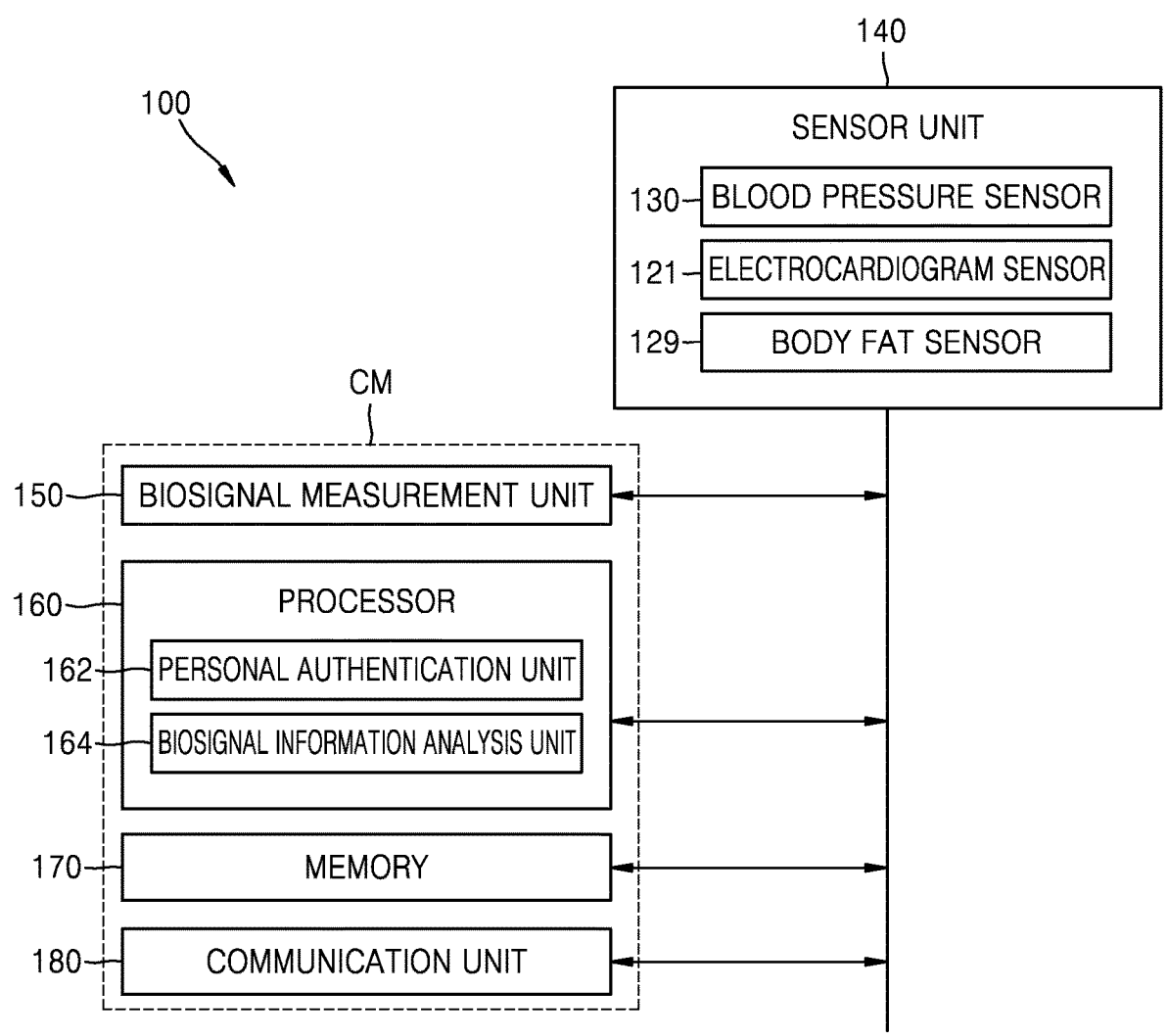
FIG. 5 is a block diagram of a detachable biosignal complex sensor according to an exemplary embodiment.
Figure 6:
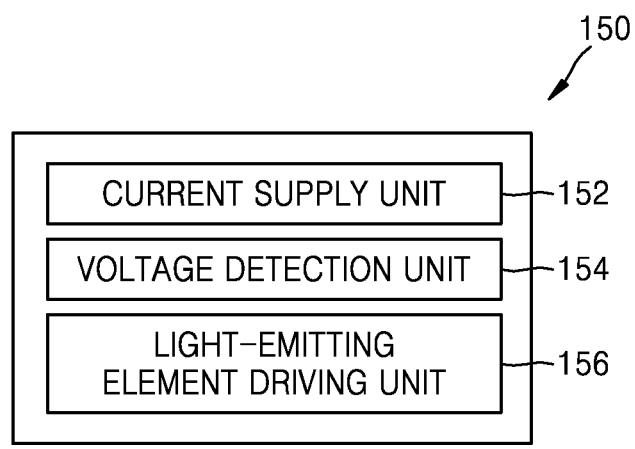
FIG. 6 is a block diagram of a biosignal measurement unit of FIG. 5.
Figure 7:
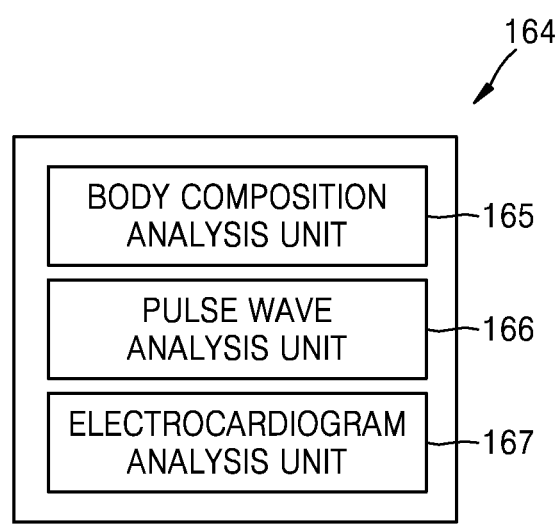
FIG. 7 is a block diagram of a biosignal information analysis unit of FIG. 5.

FIG. 5 is a block diagram of the detachable biosignal complex sensor 100 according to the exemplary embodiment, FIG. 6 is a block diagram of a biosignal measurement unit 150 of FIG. 5, and FIG. 7 is a block diagram of a biosignal information analysis unit 164 of FIG. 5.

As described above, the blood pressure sensor 130, the ECG sensor 121, and the body fat sensor 129, which constitute a sensor unit 140 (e.g., sensor) of the detachable biosignal complex sensor 100, are exposed to the outer surface of the clip type structure 110.

The blood pressure sensor 130 may include a light-emitting element and a light-receiving element. The blood pressure sensor 130 may irradiate light on the subject and sense an optical signal that is reflected or scattered from the subject. For example, the blood pressure sensor 130 may detect a laser speckle that is generated by scattering of a laser beam irradiated on the subject. According to an exemplary embodiment, the term laser speckle refers to irregular patterns that are generated by interference or scattering when a coherent laser beam is irradiated on a scattering body. The blood pressure sensor may detect an optical signal corresponding to laser speckle.

The ECG sensor 121 is configured to sense electrical activity of a heart. The ECG sensor 121 may detect a slight electrical signal that is sensed from a skin when myocardium is depolarized at every heartbeat.

The body fat sensor 129 may apply current to the subject and detect an output voltage from the subject.

A circuit module CM, which senses a biosignal from the subject and performs signal processing on the sensed biosignal, may be embedded in a first plate 112 and a second plate 114, which constitutes the clip type structure 110.

The circuit module CM may include a biosignal measurement unit 150 (e.g., biosignal measurer) that provides the sensor unit 140 with an input for sensing a biosignal and performs measurement on an output of the sensor unit 140, and a processor 160 that performs a variety of processing for biosignal analysis according to the measurement result. The processor 160 may include a personal authentication unit 162 (e.g., personal authenticator) that performs personal authentication based on a sensed ECG signal, and a biosignal information analysis unit 264 that analyzes biosignal information by using personal-authenticated user information and sensed biosignal. In addition, the circuit module CM may further include a memory 170 and a communication unit 180 (e.g., communicator).

As illustrated in FIG. 6, the biosignal measurement unit 150 may include a current supply unit 152 (e.g., current supplier), a voltage detection unit 154 (e.g., voltage detector), and a light-emitting element driving unit 156 (e.g., light-emitting element driver). The current supply unit 152 may supply current to an input electrode of the body fat sensor 129. The voltage detection unit 154 may measure a voltage between output electrodes of the body fat sensor 129. The light-emitting element driving unit 156 may apply a voltage for driving the light-emitting element of the blood pressure sensor 130. In addition, the biosignal measurement unit 150 may further include an amplifier that amplifies an electrical signal detected by the ECG sensor 121.

The personal authentication unit 162 may perform personal authentication based on a sensed ECG signal. Specifically, the personal authentication unit 162 may determine whether the subject is a registered user, based on the ECG signal sensed by the ECG sensor 121. When it is determined that the subject is the registered user, the personal authentication unit 162 may transmit a control signal for driving the blood pressure sensor 130 or the body fat sensor 129 to the biosignal measurement unit 150. In addition, when the biosignal is sensed by the sensor unit 140, the personal authentication unit 162 may transmit a related signal to the biosignal information analysis unit 164 (e.g., biosignal information analyzer) so as to perform biosignal information analysis by using the registered user information. For this purpose, the personal authentication unit 162 may perform ECG signal measurement on the user who will use the detachable biosignal complex sensor 100, and input the measurement result and related user information to the memory 170 in advance.

The biosignal information analysis unit 164 may analyze biosignal information by using the signals sensed by the blood pressure sensor 130, the ECG sensor 121, and the body fat sensor 129. As illustrated in FIG. 7, the biosignal information analysis unit 164 may include a body composition analysis unit 165 (e.g., body composition analyzer), a pulse wave analysis unit 166 (e.g., pulse wave analyzer), and an ECG analysis unit 167 (e.g., ECG analyzer).

The body composition analysis unit 165 may calculate body impedance based on the input current applied to the body fat sensor 129 and the detected output voltage, and analyze the body composition based on the calculated body impedance.

The pulse wave analysis unit 166 may detect a pulse wave signal by analyzing an optical signal sensed by the blood pressure sensor 130, and calculate a variety of types of biosignal information from the detected pulse wave signal.

Specifically, the pulse wave analysis unit 166 may analyze a change in the intensity of the optical signal detected by the light-receiving element of the blood pressure sensor 130 with respect to time. The pulse wave analysis unit 166 may acquire a biosignal by analyzing laser speckle fluctuation corresponding to a change in a volume of a blood vessel (for example, radial artery) of an object. The acquired biosignal may be a PPG signal converted based on a correlation between the analyzed speckle fluctuation and the volume change. The pulse wave analysis unit 166 may analyze various parameters included in a PPG pulse wave signal by analyzing wavelength characteristics of the PPG pulse wave signal. For example, the pulse wave analysis unit 166 may calculate a delay time between pulse wave signals and calculate a pulse transit time (PTT) from the calculated delay time. During this process, various digital signal processing algorithms, such as a noise removal algorithm or a differential signal extraction algorithm, may be used. The extracted pulse wave signal analysis result may be used as an index for analyzing a variety of biosignal information. That is, the biosignal information may be analyzed by using a predetermined algorithm configured to calculate a variety of biosignal information from analyzed PTT. For example, a vascular compliance, a blood flow rate, arterial stiffness, a systolic blood pressure, or a diastolic blood pressure may be estimated.

The ECG analysis unit 167 may analyze an ECG based on an electrical signal sensed by the ECG sensor 121. A healthy heart has an orderly depolarization waveform that spreads over a ventricle from a signal output from a sinoatrial node. A waveform of a small voltage sensed by two electrodes shows an entire rhythm of a heart. From the waveform, a rate or a consistency of a heartbeat may be analyzed, and damage to a specific part of myocardium may be analyzed.

The memory 170 may store a program to control processing operations and other operations of the processor 160, and may store input/output data. For example, a program for the personal authentication and the biosignal information analysis to be performed by the processor 160 may be stored in a code form. In addition, the memory 170 may store the measurement results of the sensor unit 140 and the user information, which may be used for processing operations by he processor 160.

The memory 170 may include a storage medium selected from among a flash memory, a hard disk, a multimedia card micro type memory, a card type memory (for example, SD or XD memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk.

The communication unit 180 may transmit the analysis result to an external device by wire or wireless. The external device may be a medical device that uses the analyzed biosignal information, a printer that prints the results, or a display device that displays the analysis results. In addition, the communication unit 180 may be a smartphone, a mobile phone, a personal digital assistant (PDA), a laptop computer, a personal computer (PC), or other mobile or non-mobile computing devices, but is not limited thereto.

The communication unit 180 may be connected to the external device by wire or in a wireless fashion. For example, the communication unit 180 may communicate with the external device through a Bluetooth communication scheme, a Bluetooth Low Energy (BLE) communication scheme, a near field communication (NFC) scheme, a WLAN (WiFi) communication scheme, a Zigbee communication scheme, an infrared data association (IrDA) communication scheme, a Wi-Fi Direction (WFD) communication scheme, an Ultra WideBand (UWB) communication scheme, an Ant+ communication scheme, or a WiFi communication scheme, but is not limited thereto.

Figure 8:
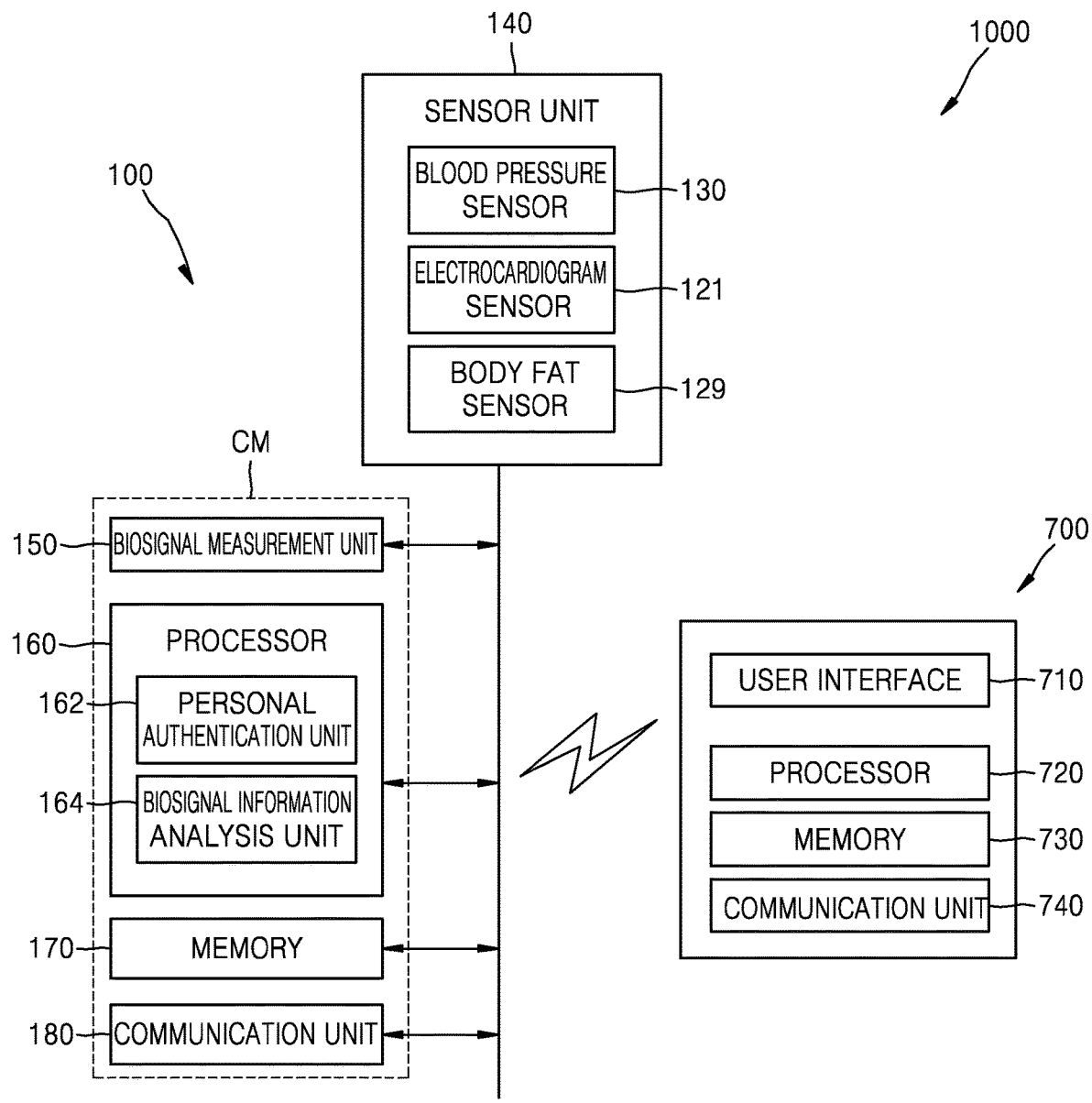
FIG. 8 is a block diagram of a biosignal information detection system according to an exemplary embodiment.

FIG. 8 is a block diagram of a biosignal information detection system 1000 according to an exemplary embodiment.

The biosignal information detection system 1000 may include a detachable biosignal complex sensor 100 and an external electronic device 700 capable of communicating with the detachable biosignal complex sensor 100.

The external electronic device 700 may include a user interface 710 that receives an execution command for the detachable biosignal complex sensor 100 and outputs a command execution result, and a communication unit 740 (e.g., communicator) that communicates with the detachable biosignal complex sensor 100. In addition, the external electronic device 700 may include a processor 720 and a memory 730.

The external electronic device 700 may be a wrist watch type device as illustrated in FIG. 3A, or may be a smartphone, a mobile phone, a PDA, a laptop computer, a PC, or other mobile or non-mobile computing devices, but exemplary embodiments are not limited thereto.

Figure 9:
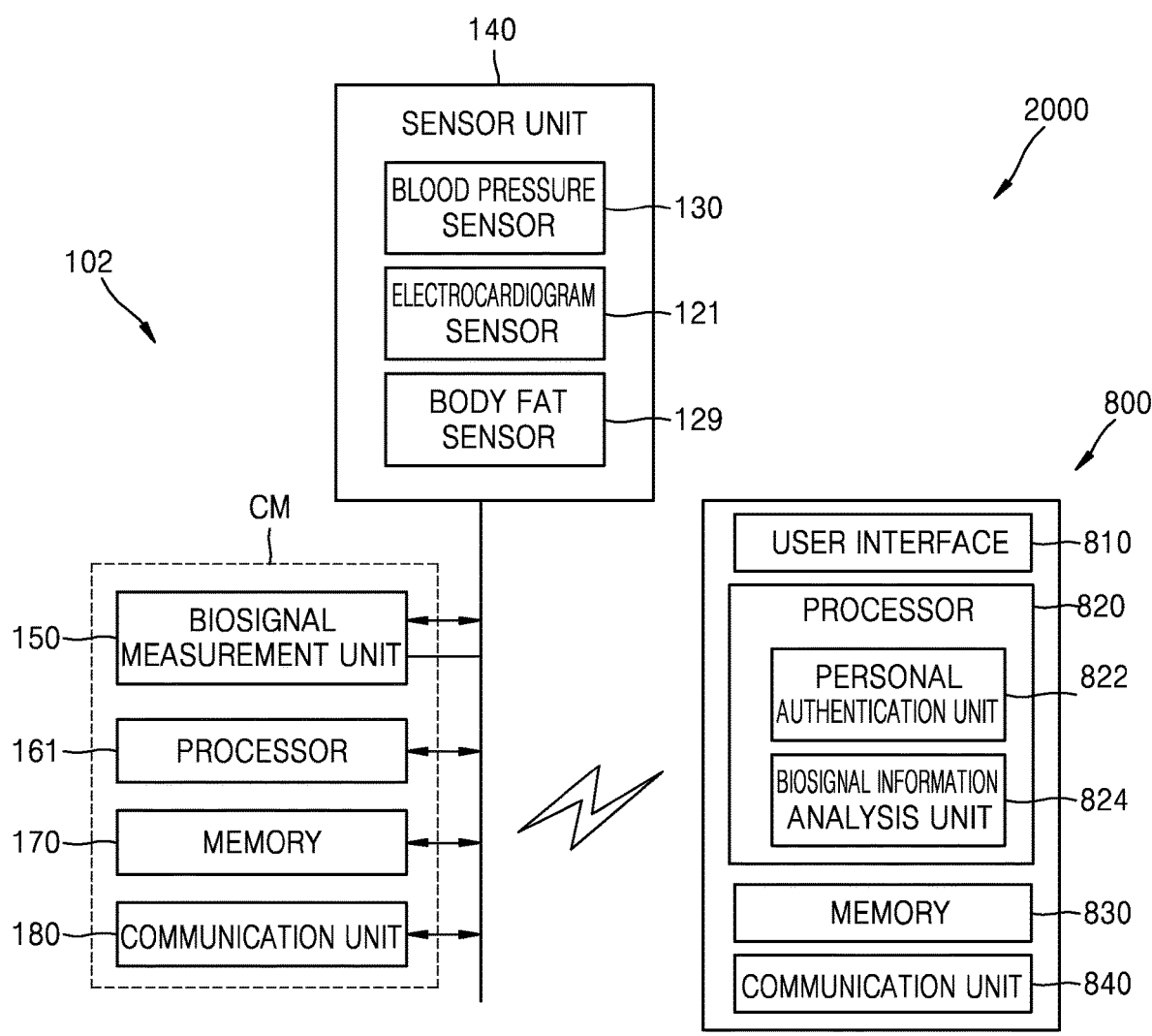
FIG. 9 is a block diagram of a biosignal information detection system according to another exemplary embodiment.

FIG. 9 is a block diagram of a biosignal information detection system 2000 according to another exemplary embodiment.

The biosignal information detection system 2000 according to the present exemplary embodiment may include a detachable biosignal complex sensor 102 and an external electronic device 800. The biosignal information detection system 2000 differs from the biosignal information detection system 1000 of FIG. 8 in that the functions performed by a personal authentication unit 822 and a biosignal information analysis unit 824 are performed in the external electronic device 800.

The detachable biosignal complex sensor 102 may include a sensor unit 140, a biosignal measurement unit 150, a processor 161, a memory 170, and a communication unit 180.

The external electronic device 800 may include a user interface 810 that receives an execution command for the detachable biosignal complex sensor 102 and outputs a command execution result, a processor 820 including a personal authentication unit 822 and a biosignal information analysis unit 824, a memory 830, and a communication unit 840.

The appearances and/or the functions of the detachable biosignal complex sensors 100, 101, and 102 have been described with reference to the block diagrams and may be mutually combined.

Figure 10:
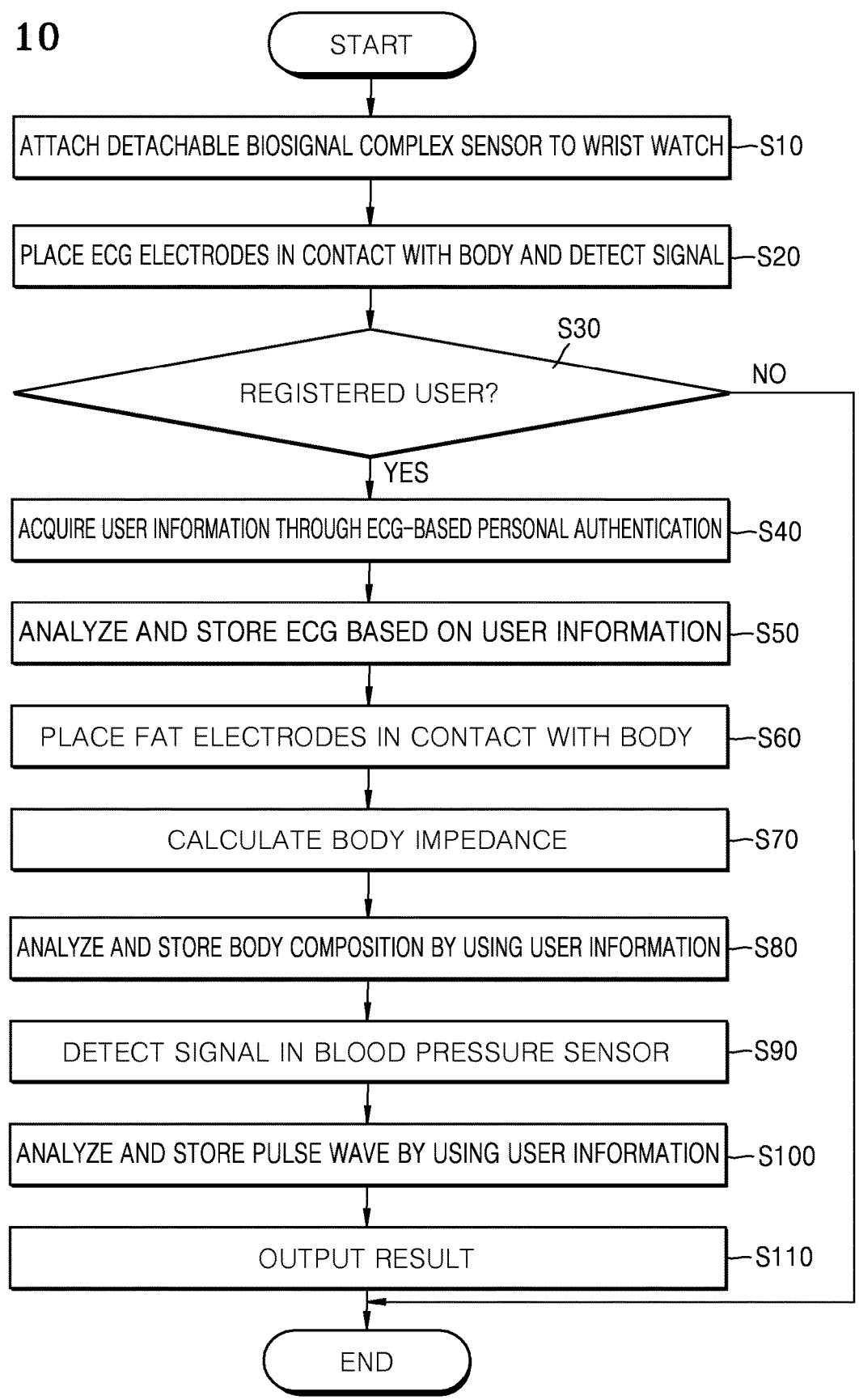
FIG. 10 is a flowchart of a method of detecting biosignal information by using a detachable biosignal complex sensor, according to an exemplary embodiment.

FIG. 10 is a flowchart of a method of detecting biosignal information by using a detachable biosignal complex sensor, according to an exemplary embodiment.

The method of detecting the biosignal information according to the exemplary embodiment may be performed by the above-described detachable biosignal complex sensor or the biosignal information detection system including the same.

Referring to FIG. 10, in operation S10, the detachable biosignal complex sensor is attached to a wrist watch. The wrist watch, to which the detachable biosignal complex sensor is attached, may be worn by a user, that is, a subject.

Figure 11:
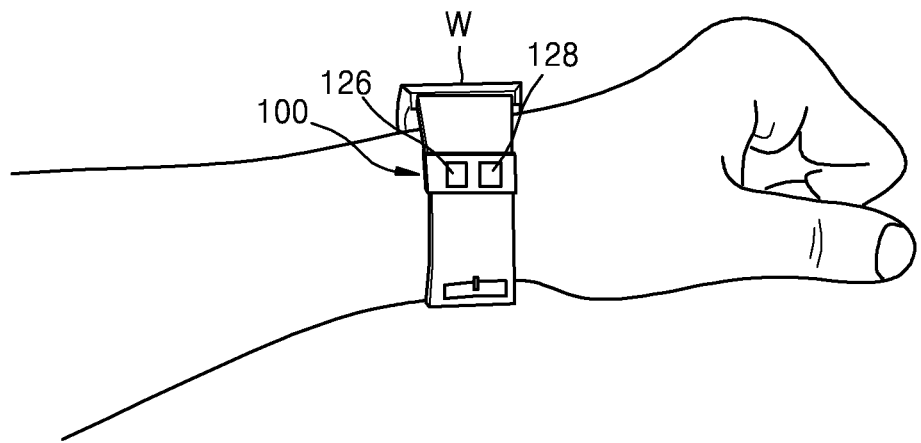
FIG. 11 is a diagram illustrating a case where a user wears a wrist watch to which a detachable biosignal complex sensor is attached.

FIG. 11 is a diagram illustrating a case where the user wears the wrist watch W to which the detachable biosignal complex sensor 100 is attached.

In operation S20, when the user wears the wrist watch W, the ECG sensor 121 of the detachable biosignal complex sensor 100 contacts a body of the subject, and an ECG signal is sensed by the ECG sensor 121.

In operation S30, when the ECG signal is sensed, it is determined whether the subject is a registered user. In operation S40, when it is determined that the subject is not the registered user, the process is ended, and when it is determined that the subject is the registered user, user information is acquired through personal authentication based on ECG.

In order to acquire such personal authentication, a user may previously store information about the user who will use the detachable biosignal complex sensor 100.

Figure 12:
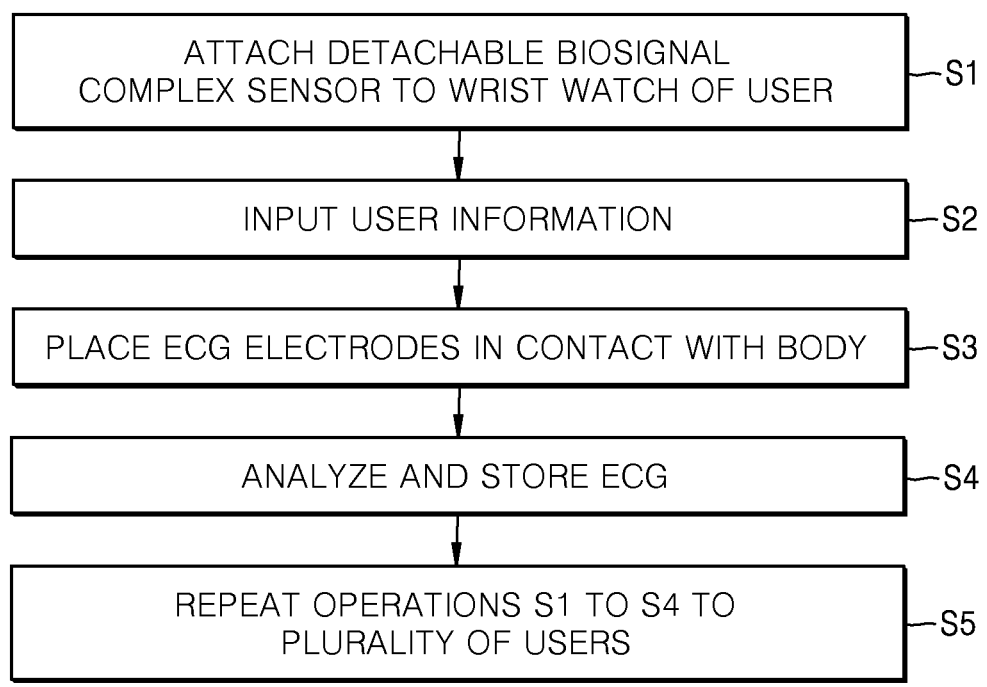
FIG. 12 is a flowchart of a process of registering a user in a detachable biosignal complex sensor.

FIG. 12 is a flowchart of a process of registering a user in a detachable biosignal complex sensor.

In operation S2, the detachable biosignal complex sensor is attached to the wrist watch W, and the user information is input. The user refers to a subject from which biosignal information is to be measured. The user information may be weight, age, and gender of the subject.

In operation S3, the body of the subject contacts the ECG sensor. For example, the body of the subject may contact the ECG electrodes in such a manner that the subject wears the wrist watch W to which the detachable biosignal complex sensor is attached.

In operation S4, a signal from the ECG electrodes is analyzed and the analysis result is stored.

In operation S5, operations S1 to S4 may be repeated for a plurality of users.

Returning to FIG. 10, in operation S50, after the user information is acquired, ECG analysis is performed and the ECG analysis result is stored.

In operations S60 and S70, the body of the subject contacts the body fat electrodes, and body impedance is calculated.

Figure 13:
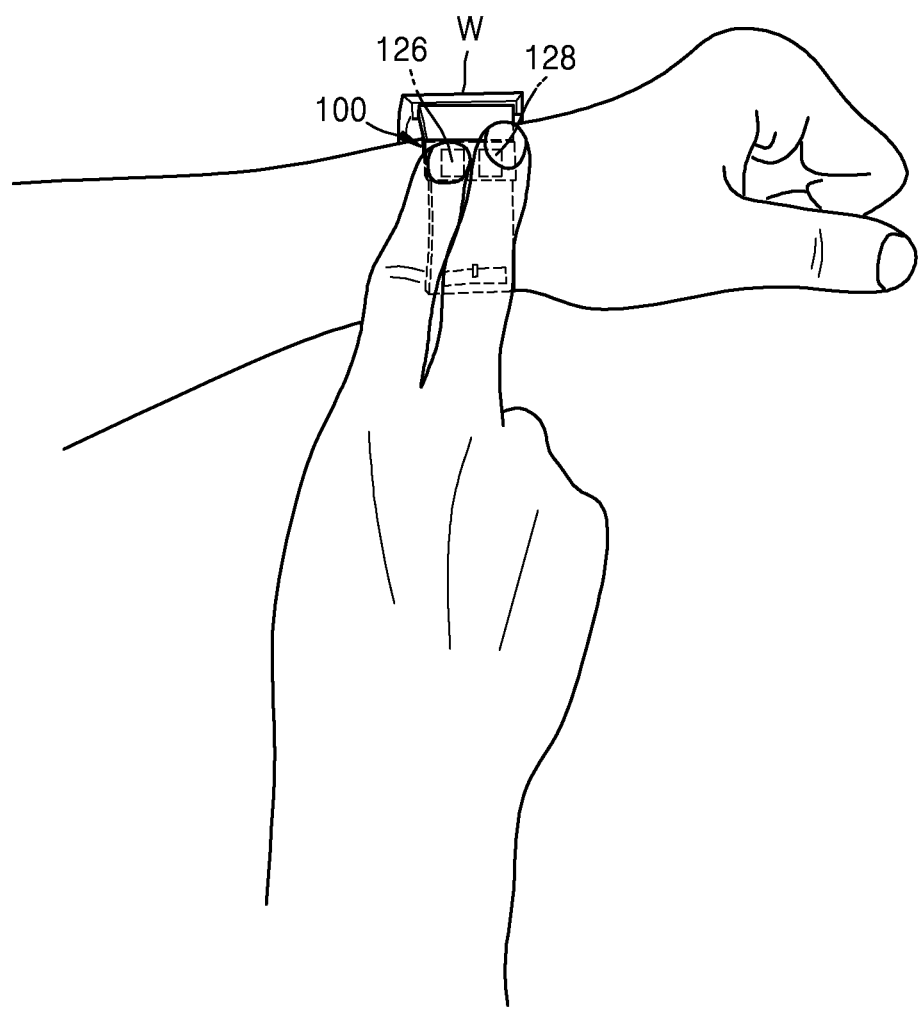
FIG. 13 is a diagram illustrating a case where a user who wears a wrist watch to which a detachable biosignal complex sensor is attached contacts a plurality of electrodes so as to analyze his or her body fat.
Figure 14:
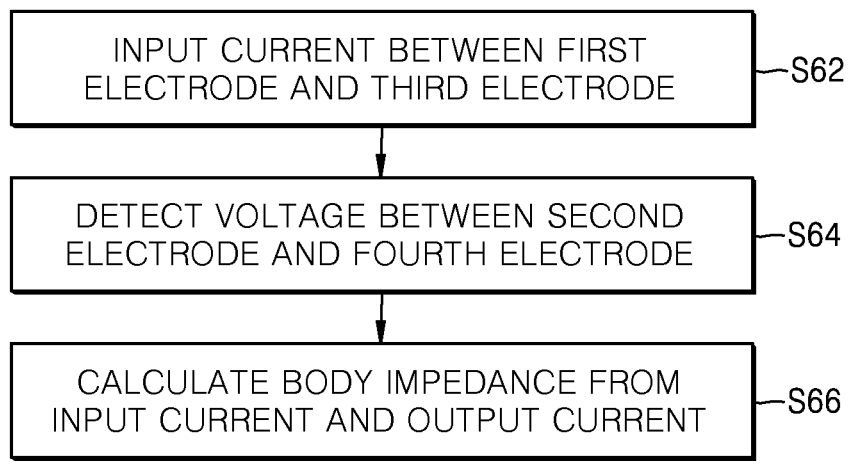
FIG. 14 is a flowchart of a process of analyzing body fat by using a body fat sensor in a detachable biosignal complex sensor.

FIG. 13 is a diagram illustrating a case where the user who wears the wrist watch W to which the detachable biosignal complex sensor 100 is attached contacts a plurality of electrodes so as to analyze his or her body fat, and FIG. 14 is a flowchart of a process of analyzing the body fat by using the body fat sensor.

As illustrated in FIG. 13, two fingers of the user may contact the third and fourth electrodes 126 and 128. The body part contacting the third and fourth electrodes 126 and 128 is merely exemplary, and is not limited to the above example of two fingers.

In operations S62 and S64, in a state in which the first and second electrodes 122 and 124 come into contact with the wrist of the user and the third and fourth electrodes 126 and 128 come into contact with the fingers of the user, current is input between the first electrode 122 and the third electrode 126, and a voltage between the second electrode 124 and the fourth electrode 128 is detected. In operation S66, body impedance is calculated from the input current and the output voltage.

The first and third electrodes 122 and 126 may serve as input electrodes for the input of the current, and the second and fourth electrodes 124 and 128 may serve as output electrodes for the detection of the voltage, but the electrodes 122, 124, 126, and 128 are not limited thereto. The input electrodes and the output electrodes may be set as another combination.

In operation S80, when the body impedance is calculated, the body composition may be analyzed using the user information and the analysis result may be stored. The body composition may include, for example, body fat, body water, muscle strength, or edema.

In operations S90 and S100, a signal from the blood pressure sensor is detected and a pulse wave is analyzed from the detected signal. In addition, in this operation, a variety of biosignal information may be analyzed using the pulse wave.

Figure 15:
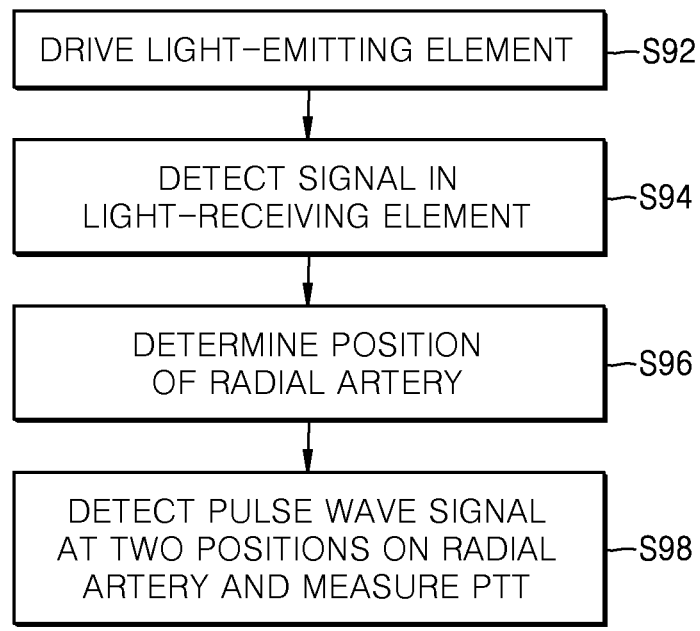
FIG. 15 is a flowchart of a process of analyzing biosignal information by using a blood pressure sensor in a detachable biosignal complex sensor.
Figure 16:
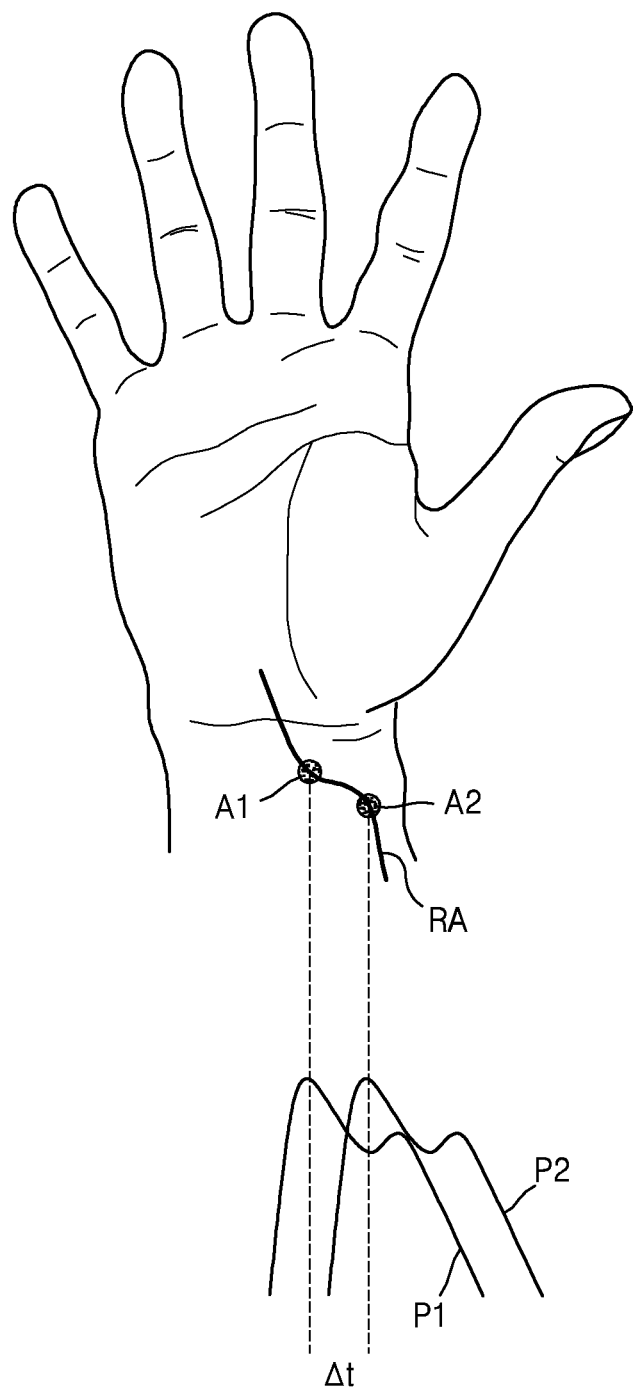
FIG. 16 is a conceptual diagram of a method of analyzing a pulse wave signal in the flowchart of FIG. 15.

FIG. 15 is a flowchart of a process of analyzing biosignal information by using the blood pressure sensor, and FIG. 16 is a conceptual diagram of a method of analyzing a pulse wave signal in the flowchart of FIG. 15.

In operation S92, the light-emitting element of the blood pressure sensor is driven to irradiate light on the subject. In operation S94, an optical signal reflected or scattered from the subject is detected in the light-receiving element.

In operation S96, a position of a radial artery is determined. When a pulse wave is measured on a skin surface of the wrist, through which a radial artery passes, the influence of external factors causing an occurrence of measurement error in a thickness of a skin tissue inside the wrist may be reduced. It is known that the radial artery is a blood vessel at which a blood pressure can be measured more accurately than other types of blood vessels inside the wrist. Generally, since the position of the radial artery of the subject can be empirically estimated in advance, an exemplary embodiment may make it possible to perform a more accurate position control from the biosignal sensed by the light-receiving element of the blood pressure sensor.

In operation S98, pulse signals are detected at two positions on the radial artery and a PTT is measured. As illustrated in FIG. 16, a time delay Δt is analyzed by comparing waveforms of two pulse signals P1 and P2 detected at two positions A1 and A2 on a radial artery RA. The time delay Δt is a parameter related to PTT information, and the PTT may be analyzed from the time delay Δt.

A variety of biosignal information may be analyzed using the analyzed pulse wave signal waveforms, the PTT information, or the like. The biosignal information may include a vascular compliance, a blood flow rate, arterial stiffness, a systolic blood pressure, or a diastolic blood pressure. In addition, the biosignal information may include information regarding whether a current blood pressure state is normal or abnormal.

In the above description of certain exemplary embodiments, the order of the ECG analysis, the body composition analysis, and the pulse wave analysis is merely exemplary, and is not limited thereto. That is, the above-described order may be reversed, or certain operations or features may be omitted according to various criteria. In addition, the case where the detachable biosignal complex sensor is attached to the wrist watch and is worn on a wrist of a user has been described above, but the exemplary embodiments are not limited thereto. For example, the detachable biosignal complex sensor may be detachably attached to various wearable devices.

Since the detachable biosignal complex sensor according to exemplary embodiments may be attached to the wrist watch or the like only when the detachable biosignal complex sensor is being used, users do not have to experience the inconvenience of having to wear the biosignal sensor even when unnecessary.

In addition, the detachable biosignal complex sensor according to exemplary embodiments may have the personal authentication function. It is possible to measure biosignals of a plurality of users and analyze biosignal information thereof by using the personal authentication function.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A detachable biosignal sensor comprising:
   a clip type structure comprising:
      a circuit module configured to receive a biosignal of a subject and perform signal processing on the biosignal,
      a first plate, and
      a second plate comprising an edge which is directly and rotatably connected to an edge of the first plate to switch between an open state and a closed state, so that the clip type structure is configured to be fastened to a strap of a wearable device in the closed state in which a surface of the first plate is disposed in opposition to and in parallel with a surface of the second plate to allow the strap to be inserted into a gap between the surface of the first plate and the surface of the second plate; and
   a sensor and electrodes provided on outer surfaces of the first plate and the second plate and configured to obtain the biosignal and transmit the obtained biosignal to the circuit modules,
   wherein the clip type structure is separately provided from the strap to be attachable to and detachable from the strap, and configured to be fastened to the strap in the closed state to allow either the first plate or the second plate of the clip structure to be in contact with a wrist of the subject while the biosignal is measured.

2. The detachable biosignal sensor of claim 1, wherein the electrodes include:
   a first electrode and a second electrode on the first plate; and
   a third electrode and a fourth electrode on the second plate.

3. The detachable biosignal sensor of claim 2, wherein the first electrode and the second electrode are configured to function as an electrocardiogram sensor, and
   the first electrode, the second electrode, the third electrode, and the fourth electrode are configured to function as a body fat sensor.

4. The detachable biosignal sensor of claim 1, wherein the clip type structure provides the gap between the first plate and the second plate to allow the strap to be inserted into the gap in a direction perpendicular to a longitudinal axis of the strap.

5. The detachable biosignal sensor of claim 1, wherein the sensor comprises a light-emitting element configured to emit light and a light-receiving element configured to receive light, wherein the biosignal is obtained based on the emitted and received light.

6. The detachable biosignal sensor of claim 1, wherein the sensor comprises a light-receiving element configured to receive light, and a first light-emitting element and a second light-emitting element which are respectively positioned on opposite sides of the light-receiving element and configured to emit light, wherein the biosignal is obtained based on the emitted and received light.

7. The detachable biosignal sensor of claim 3, wherein
   the sensor comprises a light-receiving element configured to receive light, and a first light-emitting element and a second light-emitting element which are respectively positioned on opposite sides of the light-receiving element and configured to emit light, wherein the biosignal is obtained based on the emitted and received light,
   the first electrode and the second electrode are spaced apart from each other in a first direction, and
   the first light-emitting element, the light-receiving element, and the second light-emitting element are spaced apart from one another between the first electrode and the second electrode in a second direction perpendicular to the first direction.

8. The detachable biosignal sensor of claim 1, wherein the clip type structure comprises a flexible material.

9. The detachable biosignal sensor of claim 1, further comprising a first connection member disposed on the first plate and a second connection member disposed on the second plate, and
   wherein the first connection member is disposed apart from the second connection member in the open state, and the first connection member is disposed in contact with the second connection member in the closed state.

10. The detachable biosignal sensor of claim 9, wherein the first and second connection members comprise a magnet and magnetic material or male and female hook-and-loop fasteners.

11. The detachable biosignal sensor of claim 1, wherein the circuit module comprises:
    a personal authenticator configured to perform personal authentication based on an electrocardiogram signal of the subject and thereby generate personal-authenticated user information; and
    a biosignal information analyzer configured to analyze biosignal information of the subject by using the personal-authenticated user information and the biosignal.

12. The detachable biosignal sensor of claim 1, wherein the entire surface of the first plate is disposed in parallel with the entire surface of the second plate and faces the entire surface of the second plate, when the clip type structure is in the closed state.

13. A biosignal information detection system comprising:
    a detachable biosignal sensor comprising:
       a clip type structure comprising:
          a circuit module configured to receive a biosignal of a subject and perform signal processing on the biosignal,
          a first plate, and
          a second plate comprising an edge which is directly and rotatably connected to an edge of the first plate to switch between an open state and a closed state, so that the clip type structure is configured to be fastened to a strap of a wearable device in the closed state in which a surface of the first plate is disposed in opposition to and in parallel with a surface of the second plate to allow the strap to be inserted into a gap between the surface of the first plate and the surface of the second plate; and
       a sensor and electrodes provided on outer surfaces of the first plate and the second plate and configured to obtain the biosignal and transmit the obtained biosignal to the circuit module; and an external electronic device comprising a user interface configured to receive an execution command which commands the detachable biosignal sensor to execute a process and outputs a command execution result of the process, and a communicator configured to communicate with the detachable biosignal sensor, wherein the clip type structure is separately provided from the strap to be attachable to and detachable from the strap, and configured to be fastened to the strap in the closed state to allow either the first plate or the second plate of the clip structure to be in contact with a wrist of the subject while the biosignal is measured.

14. The biosignal information detection system of claim 13, wherein the circuit module of the detachable biosignal sensor comprises:

a personal authenticator configured to perform personal authentication based on an electrocardiogram signal of the subject and thereby generate personal-authenticated user information; and a biosignal information analyzer configured to analyze biosignal information of the subject by using the personal-authenticated user information and the biosignal.

15. The biosignal information detection system of claim 13, wherein the external electronic device comprises:

a personal authenticator configured to perform personal authentication based on an electrocardiogram signal of the subject and thereby generate personal-authenticated user information; and a biosignal information analyzer configured to analyze biosignal information of the subject by using the personal-authenticated user information and the biosignal.

* * * * *